(12) United States Patent
Meyerhoff et al.

(10) Patent No.: US 6,432,434 B1
(45) Date of Patent: Aug. 13, 2002

(54) TREATMENT OF AND/OR PROPHYLAXIS AGAINST BRAIN AND SPINAL CORD INJURY

(75) Inventors: James L. Meyerhoff, Silver Spring; Joseph Long, Clarksville; Michael Koenig, Silver Spring, all of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/556,954

(22) Filed: Apr. 21, 2000

Related U.S. Application Data

(60) Provisional application No. 60/130,452, filed on Apr. 22, 1999.

(51) Int. Cl.$^7$ ............................ A61F 13/00; A61K 9/20; A01N 37/00; A01N 31/00; A01N 43/26
(52) U.S. Cl. ..................... 424/422; 424/464; 424/449; 514/557; 514/578; 514/706; 514/886; 514/440
(58) Field of Search ................................. 424/449, 464

(56) References Cited

U.S. PATENT DOCUMENTS 5,084,481 A * 1/1992 Ulrich et al.
5,569,670 A * 10/1996 Weischer et al.
5,977,162 A * 11/1999 Seidman

* cited by examiner

*Primary Examiner*—Thurman K. Page
*Assistant Examiner*—Isis Ghali
(74) *Attorney, Agent, or Firm*—Elizabeth Arwine

(57) ABSTRACT

The administration of α-lipoic acid (αLA) and dihydrolipoic acid (DHL) both as a preventive measure before exposure to conditions which may cause damage, such as rapid changes in atmospheric pressure, and as a means of preventing or ameliorating damage arising from such injury provides benefits not currently available. The active agents may be administered systemically or to the injured tissue. For example, when there is spinal cord injury, the active agents may be administered intrathecally.

10 Claims, No Drawings

TREATMENT OF AND/OR PROPHYLAXIS AGAINST BRAIN AND SPINAL CORD INJURY

This application takes priority from Provisional Patent Application No. 60/130,452 filed Apr. 22, 1999

FIELD OF THE INVENTION

This invention relates to the field of prevention of damage arising from spinal cord injury and trauma to the brain, including that which occurs secondary to decompression sickness (DCS).

BACKGROUND OF THE INVENTION

At present, spinal injury, whether arising from trauma or disease, disables many Americans of all ages. There is need for means of effective treatment to prevent such disabilities.

Alpha lipoic acid (αLA) is an antioxidant currently used clinically to treat diabetic neuropathy. It has been shown to be clinically safe and was shown to be neuroprotective against ischemia-reperfusion injury in both the rat and the gerbil. It was also effective against NMDA and malonic acid lesions of striatum in rats. However, its effects in preventing or ameliorating damage arising because of pathologies and trauma to the spinal cord or trauma-induced injury to the brain, including spinal cord injury secondary to decompression sickness (DCS), has not been known.

DCS-induced spinal injury is often associated with hemorrhage into the spinal cord. Extravasated hemoglobin releases iron, which is deposited in neural tissues where it is neurotoxic due to free radical formation and lipid peroxidation, resulting in cavitation and gliosis. The interaction with the superoxides and peroxides with cell membrane components can cause protein chain polymerization, destruction of sulfhydryl groups and degradation of DNA and amino acids. Hemoglobin has also been shown to potentiate excitatory amino acid-induced neurotoxic injury in cortical cell culture. There is need for agents which effectively protect against this pathological cascade.

Presently, post-injury treatment of spinal cord injury is most likely to include administration of the steroid methylprednisolone for 24 to 48 hours to reduce swelling and inflammation. In patients with accident-related acute spinal cord injury, clinical outcome at 6 months was improved in those receiving this steroid within eight hours of injury compared with placebo-treated patients. Unfortunately, there is some evidence that glucocorticoids (GC's) can exacerbate the excitotoxic phase of neural injury. Postulated mechanisms of GC-mediated synergy with excitotoxic effects of glutamic acid include: (1) glucocorticoides inhibit reuptake inactivation of synaptic glutamic acid, thereby increasing synaptic glutamic acid levels and/or (2) glucocorticoids inhibit calcium removal from the postsynaptic neuron.

SUMMARY OF THE INVENTION

It is the purpose of this invention to provide means to prevent neuronal damage arising because of injury to the spinal cord or brain. The administration of α-lipoic acid (αLA) and dihydrolipoic acid (DHL) both as a preventive measure before exposure to conditions which may cause damage, such as rapid changes in atmospheric pressure, and as a means of preventing or ameliorating damage arising from such injury provides benefits not currently available. The active agents may be administered systemically or to the injured tissue. For example, when there is spinal cord injury, the active agents may be administered intrathecally.

DETAILED DESCRIPTION OF THE INVENTION

There are many instances when an injury may not be immediately life-threatening, but may have potential to cause severe disability. Injuries such as those arising from penetrating injuries, exposure to blast, blunt trauma, falls and vehicular accidents as well as spinal cord and brain injury secondary to systemic phenomena such as decompression sickness are examples of instances when use of αLA and dihydrolipoic acid in accord with the teachings of this disclosure would be appropriate. Conditions such as herniated discs or degenerative diseases such as amyotrophic lateral sclerosis and multiple sclerosis are pathological processes whose deleterious effects may be ameliorated by practice of the methods of the invention.

One great advantage associated with the use of αLA is that it may be administered orally, is readily absorbed and is converted to the more potent neuroprotectant, dihydrolipoic acid. It is well tolerated in man and may be given prophylactically to soldiers at risk for spinal cord injury.

The use of α-lipoic acid can be demonstrated for efficacy in preventing spinal cord injury using the following models: (1) Dynorphin-A induced ischemia, (2) animal models of spinal cord injury secondary to decompression sickness and (3) weight-drop models of spinal cord injury.

Since decompression sickness-induced spinal cord injury can be modelled by placing rats in a hyperbaric chamber, it is possible to use such a model to screen for clinically-available compounds which might mitigate risk in a vulnerable population. However, a model of spinal injury with less variability and higher throughput provides a more efficient way to test therapeutic concepts. The methods of the invention include prophylaxing against damage arising from spinal cord injury or pathology comprising administration of a neuronal protective amount of at least one agent chosen from among dihydrolipoic acid, α-lipoic acid or an ester of α-lipoic acid before exposure to circumstances which give rise to spinal cord injury. If damage has occurred, it is appropriate to treat the vertebrate who has incurred spinal cord or brain injury or pathology to prevent neuronal damage arising from said injury or pathology by administering a neuronal damage preventing effective amount of at least one agent chosen from among dihydrolipoic acid, α-lipoic acid or an ester of α-lipoic acid.

EXAMPLE 1

Rats were injected with 20 μmoles of dynorphin A in combination with DMSO (vehicle only) or dynorphin A (Dny) with 5 μmoles of dihydrolipoate in DMSO. The DMSO (control) and the DMSO with dihydrolipoate (DHL/DMSO) were administered as 2 hour pretreatment before administration of the dynorphin A and as cotreatment with dynorphin A. All rats were flaccidly paralyzed 10 minutes following dynorphin a injections. All injections were administered intrathecally. Table 1 gives the results.

TABLE 1

| | Neurological score | | | |
|---|---|---|---|---|
| | 2 hrs. | | 24 hrs. | |
| | Dny, Veh* | Dny, Veh, DHL# | Dyn, Veh* | Dyn, Veh, DHL# |
| animals | n = 8 | n = 9 | n = 7 | n = 9 |
| 4 (normal) | — | 2 | — | 4 |
| 3 | — | 3 | — | 3 |
| 2 | — | 2 | — | — |
| 1 | 2 | 1 | 1 | 2 |
| 0 | 6 | 1 | 6 | — |

*is dynorphin and vehicle, #is dynorphin, vehicle and DHL and wherein 4 is normal and 0 is flaccid paralysis.

Because α-lipoic acid is converted in the body to dihydrolipoate (DHL), which is highly effective, the DHL can be given when an immediate response is desired. When a prolonged response is desired or it is desirable to administer an active agent prophylactically, the αLA is administered.

The αLA can be administered by mouth. The αLA and DHL can also be administered rectally (for example, as a suppository), parenterally, or by application to the mucosa such as by buccal or intranasal administration. It may also be delivered transdermally. Patch technique is particularly useful for this means of administration. The DHL is a lipophilic compound and may be administered directly to the tissue as, for example, to the brain in intracranial surgery, in the usual carriers for lipophilic drugs. Examples of such carriers are glycols such as polypropylene glycol, polyethylene glycol, ethanol, DMSO and cyclodextrins (especially the amorphous cyclodextrins). Cyclodextrins will pass through the buccal or nasal mucosa into the circulation easily. This method is particularly appropriate for administration as a means of avoiding intravenous administration while bypassing the liver. Other vehicles that should be considered include fatty acid esters of polyoxyethylene sorbital (Tweens) or sorbitan (Spans) for preparation of emulsions. Compositions can be administered is directly to the tissue during surgery in the form of sprays or by injection as when given intrathecally. DHL is reactive and must be stored very carefully away from light. It is often vialed under argon.

Administration of the esters of the acid may also be advantageous. Appropriate esters include those commonly used as protective groups and include, but are not limited to, alkyl, phenyl and phenylalkyl esters. The esters may be substituted with, for example, hydroxy, alkoxy and halo groups.

One means of topical application is the use of skin patches impregnated with the active agent. This means of delivery is advantageous since it is non-invasive and easily administered by relatively unskilled care providers.

There are patients, such as those who suffer from seizures or who are not sufficiently responsive, to whom compositions of αLA and DHL may be beneficially administered by rectum in retention enemas or suppositories. The α-lipoic acid may be administered in food.

EXAMPLE 2

Preparation for application to tissue:

| Ingredient | % w/w |
|---|---|
| DHL | 0.05% |
| polypropylene glycol | 13.0% |
| Water | 86.95% |

EXAMPLE 3

Preparation for intrathecal injection:

| Ingredient | Amount |
|---|---|
| DHL | 100 μmoles |
| Ethanol | 5 ml. |
| Phosphate buffered saline | Add to 50 ml. |

EXAMPLE 4

Water, 100 ml, is mixed with 7 g. β-hydroxypropyl cyclodextrin and .05 g. α-lipoic acid. Fill ampules with the solution and sterilize. This preparation may be added to solutions for administration to the mucosa, for oral administration, or for parenteral administration.

EXAMPLE 5

An cyclodextrin/DHL containing 0.05 g. DHL preparation is prepared as above. The material is freeze-dried and placed in sterile ampules.

EXAMPLE 6

The preparation of Example 2 is diluted with 100 ml water. The preparation is sprayed into the intracranial cavity during and after surgery.

When given in tablet form, additional inerts such as starches, sugars, flavoring agents and preservatives may be added. When DHL is administered parenterally, solutions of 0.05 to 5 nM may be administered. Capsules or tables containing about 50 to 600 mg α-LA may be administered orally, A preferred dosage range of α-LA is about 50 to 3000 mg/da. Dosage of DHL is 10% to about 50% that of α-LA.

Patches for administration of the active agents may be formulated as adhesive patches containing the active agent. For example, the patch may be a discoid in which a pressure-sensitive silicone adhesive matrix containing the active agent may be covered with a non-permeable backing. The discoid may either contain the active agent in the adhesive or may be attached to a support made of material such as polyurethane foam or gauze that will hold the active agent. When patches are used in treating animals, the area must be shaved or plucked. In all instances, the area to which the patch is applied should be cleaned carefully before application.

EXAMPLE 7

A patch composed of trilaminate of an adhesive matrix sandwiched between a non-permeable backing and a protective covering layer is prepared in the following manner:

To a pressure-sensitive silicone adhesive composition BIOPSA™ q7-2920 (Dow Corning Corporation, Midland, Mich., U.S.A.) In cyclohexane (50% w/v) is added sufficient α-lipoic acid to provide a 5% α-LA composition. The adhesive is applied to a polyester film to provide in successive layers about 5 mg of active agent per cm$^2$. Patches should be covered with a protective layer which will be removed before application.

Patches may be prepared containing permeation enhancers such as butylated hydroxyanisole, or butylated hydroxytoluene.

The α-lipoic acid and esters thereof and DHL may be given in combination with other free radical scavengers with (1) differing mechanisms of action such as coenzyme Q or nitrones or with (2) other classes of neuroprotectants with fundamentally different mechanisms such as the neurotrophic factors (brain-derived neurotrophic factor, nerve growth factor, neurotrophins and/or the neuroprotective endogenous TRH analog, pyro Glu-Glu-Pro, known by its abbreviation, EEP).

What we claim is:

1. A method of treating a vertebrate who has incurred spinal cord or brain injury due to trauma or changes in atmospheric pressure to prevent neuronal damage arising from said injury or pathology comprising administering to said vertebrate a neuronal damage-preventing effective amount of at least one active agent selected from the group consisting of dihydrolipoic acid, α-lipoic acid or an ester of α-lipoic acid to the vertebrate who is suffering from injury or pathology of the spinal cord or brain.

2. A method of claim 1 wherein the active agent administered is dihydrolipoic acid.

3. A method of claim 2 wherein the active agent is administered intrathecally.

4. A method of claim 1 wherein the active agent is α-lipoic acid or an ester of α-lipoic acid.

5. A method of claim 4 wherein the active agent is administered orally.

6. A method of claim 1 wherein the dihydrolipoic acid is administered directly to the affected tissue.

7. A method of claim 4 wherein the active agent is administered transdermally.

8. A method of claim 7 wherein the active agent is delivered by patch.

9. A method of claim 2 wherein the active agent is administered as a cyclodextrin inclusion complex.

10. The method of claim 1 wherein the injury arises from rapid changes in atmospheric pressure.

* * * * *